US012382989B2

(12) United States Patent
Dittmann et al.

(10) Patent No.: US 12,382,989 B2
(45) Date of Patent: Aug. 12, 2025

(54) AEROSOL-GENERATOR COMPRISING A PLURALITY OF ATOMISERS

(71) Applicant: Philip Morris Products S.A., Neuchatel (CH)

(72) Inventors: Leander Dittmann, Lausanne (CH); Robert Emmett, Neuchatel (CH)

(73) Assignee: Philip Morris Products S.A., Neuchatel (CH)

(*) Notice: Subject to any disclaimer, the term of this patent is extended or adjusted under 35 U.S.C. 154(b) by 333 days.

(21) Appl. No.: 17/787,776

(22) PCT Filed: Nov. 19, 2020

(86) PCT No.: PCT/EP2020/082667
§ 371 (c)(1),
(2) Date: Jun. 21, 2022

(87) PCT Pub. No.: WO2021/129986
PCT Pub. Date: Jul. 1, 2021

(65) Prior Publication Data

US 2023/0337729 A1 Oct. 26, 2023

(30) Foreign Application Priority Data

Dec. 23, 2019 (EP) ..................................... 19219432

(51) Int. Cl.
*A24F 40/05* (2020.01)
*A24F 40/10* (2020.01)
*A24F 40/44* (2020.01)
*B05B 3/14* (2006.01)

(52) U.S. Cl.
CPC .............. *A24F 40/05* (2020.01); *A24F 40/10* (2020.01); *A24F 40/44* (2020.01); *B05B 3/14* (2013.01)

(58) Field of Classification Search
CPC .......... A24F 40/05; A24F 40/10; A24F 40/44; B05B 3/14
See application file for complete search history.

(56) References Cited

U.S. PATENT DOCUMENTS

| | | | | |
|---|---|---|---|---|
| 3,938,062 | A | 2/1976 | Hopp et al. | |
| 2013/0306084 | A1* | 11/2013 | Flick | F41H 1/02 131/328 |
| 2015/0245654 | A1 | 9/2015 | Memari et al. | |
| 2015/0245655 | A1 | 9/2015 | Memari et al. | |
| 2015/0245656 | A1 | 9/2015 | Memari et al. | |
| 2015/0245657 | A1 | 9/2015 | Memari et al. | |
| 2015/0245662 | A1 | 9/2015 | Memari et al. | |
| 2015/0245663 | A1 | 9/2015 | Memari et al. | |
| 2015/0245664 | A1 | 9/2015 | Memari et al. | |
| 2015/0245665 | A1 | 9/2015 | Memari et al. | |
| 2015/0245666 | A1 | 9/2015 | Memari et al. | |
| 2015/0245667 | A1 | 9/2015 | Memari et al. | |
| 2015/0245668 | A1 | 9/2015 | Memari et al. | |
| 2015/0359266 | A1 | 12/2015 | Memari et al. | |
| 2016/0150824 | A1 | 6/2016 | Memari et al. | |
| 2016/0192712 | A1 | 7/2016 | Memari et al. | |
| 2016/0192713 | A1 | 7/2016 | Memari et al. | |
| 2017/0178884 | A1* | 6/2017 | Murtazin | G01J 3/443 |
| 2017/0280771 | A1* | 10/2017 | Courbat | B05B 17/0661 |
| 2017/0360105 | A1 | 12/2017 | Memari et al. | |
| 2017/0360106 | A1 | 12/2017 | Memari et al. | |
| 2017/0360107 | A1 | 12/2017 | Memari et al. | |
| 2017/0360108 | A1 | 12/2017 | Memari et al. | |
| 2017/0360109 | A1 | 12/2017 | Memari et al. | |
| 2017/0360110 | A1 | 12/2017 | Memari et al. | |
| 2017/0360111 | A1 | 12/2017 | Memari et al. | |
| 2017/0360112 | A1 | 12/2017 | Memari et al. | |
| 2017/0360113 | A1 | 12/2017 | Memari et al. | |
| 2017/0360114 | A1 | 12/2017 | Memari et al. | |
| 2017/0360115 | A1 | 12/2017 | Memari et al. | |
| 2017/0360116 | A1 | 12/2017 | Memari et al. | |
| 2018/0000162 | A1 | 1/2018 | Memari et al. | |

(Continued)

FOREIGN PATENT DOCUMENTS

| | | |
|---|---|---|
| CN | 106898536 A | 6/2017 |
| CN | 108095200 A | 6/2018 |

(Continued)

OTHER PUBLICATIONS

Combined Russian Notice of Allowance and Search Report issued Mar. 7, 2024 in Russian Patent Application No. 2022119691/03 (with English Translation of Category of Cited Documents), 12 pages.

(Continued)

*Primary Examiner* — Michael H. Wilson
*Assistant Examiner* — Adam Z Baratz
(74) *Attorney, Agent, or Firm* — Oblon, McClelland, Maier & Neustadt, L.L.P.

(57) ABSTRACT

An aerosol-generator for an aerosol-generating device is provided, the aerosol-generator including: a plurality of surface acoustic wave atomisers, each surface acoustic wave atomiser including: a substrate including an active surface, and at least one transducer disposed on the active surface of the substrate to generate surface acoustic waves on the active surface; an atomisation region defined between the substrates of the plurality of surface acoustic wave atomisers; and a supply element arranged to supply a liquid aerosol-forming substrate to the atomisation region. An aerosol-generating device including the aerosol-generator is also provided.

18 Claims, 8 Drawing Sheets

(56) References Cited

U.S. PATENT DOCUMENTS

| | | | |
|---|---|---|---|
| 2018/0000163 | A1 | 1/2018 | Memari et al. |
| 2018/0049474 | A1 | 2/2018 | Memari et al. |
| 2018/0049475 | A1 | 2/2018 | Memari et al. |
| 2018/0271158 | A1 | 9/2018 | Memari et al. |
| 2018/0271159 | A1 | 9/2018 | Memari et al. |
| 2018/0271160 | A1 | 9/2018 | Memari et al. |
| 2018/0271161 | A1 | 9/2018 | Memari et al. |
| 2018/0271162 | A1 | 9/2018 | Memari et al. |
| 2018/0271163 | A1 | 9/2018 | Memari et al. |
| 2018/0271164 | A1 | 9/2018 | Memari et al. |
| 2018/0271165 | A1 | 9/2018 | Memari et al. |
| 2018/0271166 | A1 | 9/2018 | Memari et al. |
| 2018/0271167 | A1 | 9/2018 | Memari et al. |
| 2018/0335280 | A1 | 11/2018 | Flick |
| 2019/0069603 | A1 | 3/2019 | Memari et al. |
| 2020/0008483 | A1 | 1/2020 | Memari et al. |
| 2020/0008484 | A1 | 1/2020 | Memari et al. |
| 2020/0008485 | A1 | 1/2020 | Memari et al. |
| 2020/0008486 | A1 | 1/2020 | Memari et al. |
| 2020/0008487 | A1 | 1/2020 | Memari et al. |
| 2020/0008488 | A1 | 1/2020 | Memari et al. |
| 2020/0008489 | A1 | 1/2020 | Memari et al. |
| 2020/0008490 | A1 | 1/2020 | Memari et al. |
| 2020/0008491 | A1 | 1/2020 | Memari et al. |
| 2020/0008492 | A1 | 1/2020 | Memari et al. |
| 2020/0022420 | A1 | 1/2020 | Memari et al. |
| 2020/0214352 | A1 | 7/2020 | Memari et al. |
| 2020/0232766 | A1 | 7/2020 | Flick |

FOREIGN PATENT DOCUMENTS

| | | | |
|---|---|---|---|
| CN | 108697178 | A | 10/2018 |
| EP | 2 870 888 | A1 | 5/2015 |
| JP | 4-189145 | A | 7/1992 |
| JP | 2003-24442 | A | 1/2003 |
| JP | 2008238058 | A | 10/2008 |
| JP | 2019-513353 | A | 5/2019 |
| RU | 2016 138 312 | A | 4/2018 |
| WO | WO 2017/167521 | A1 | 10/2017 |
| WO | WO 2019/219873 | A1 | 11/2019 |

OTHER PUBLICATIONS

International Search Report issued Jan. 12, 2021 in PCT/EP2020/082667 filed on Nov. 19, 2020, 6 pages.

Written Opinion issued Jan. 12, 2021 in PCT/EP2020/082667 filed on Nov. 19, 2020, 5 pages.

Japanese Office Action issued on Dec. 2, 2024 in Japanese Patent Application No. 2022-538380, 2 pages.

Chinese Office Action and Search Report issued Mar. 29, 2025 in corresponding Chinese Patent Application No. 202080088337.8, with English Translation, 18 pages, citing documents 15-18 thereins.

* cited by examiner

AEROSOL-GENERATOR COMPRISING A PLURALITY OF ATOMISERS

The present disclosure relates to aerosol-generators for an aerosol-generating device, the aerosol-generators each comprising a plurality of surface acoustic wave atomisers and a supply element. The present disclosure also relates to aerosol-generating devices comprising the aerosol-generators.

Aerosol-generating systems in which an aerosol-forming substrate is heated rather than combusted are known in the art. Typically in such aerosol-generating systems, an aerosol is generated by the transfer of energy from an aerosol-generator of an aerosol-generating device to an aerosol-forming substrate. For example, known aerosol-generating devices comprise a heater arranged to heat and vaporise a liquid aerosol-forming substrate.

It would be desirable to provide an aerosol-generator for an aerosol-generating device that is compact and optimised for efficiency and flexibility.

According to a first aspect of the present disclosure there is provided an aerosol-generator for an aerosol-generating device, the aerosol-generator comprising a plurality of surface acoustic wave atomisers, and a supply element. Each surface acoustic wave atomiser comprises: a substrate comprising an active surface; and at least one transducer positioned on the active surface of the substrate for generating surface acoustic waves on the active surface of the substrate. An atomisation region is defined between the substrates of the plurality of surface acoustic wave atomisers. The supply element is arranged to supply a liquid aerosol-forming substrate to the atomisation region.

The term "surface acoustic wave" is used herein to include Rayleigh waves, Lamb waves and Love waves.

Advantageously, atomising a liquid aerosol-forming substrate using a surface acoustic wave atomiser provides improved control of the atomisation process when compared to other known aerosol-generators, such as electric heaters. In other words, the surface acoustic wave atomiser of aerosol-generators according to the present disclosure provides reliable and consistent amounts of atomised liquid aerosol-forming substrate.

Advantageously, the power required by a surface acoustic wave atomiser for atomising a liquid aerosol-forming substrate is less than the power required for atomising the same amount of liquid aerosol-forming substrate using known aerosol-generators, such as electric heaters.

Advantageously, providing a plurality of surface acoustic wave atomisers may provide improved control of atomisation of the liquid aerosol-forming substrate. Advantageously, providing a plurality of surface acoustic wave atomisers directed at a single atomisation region may increase the area of the atomisation region to which surface acoustic waves are delivered. In other words, providing a plurality of surface acoustic wave atomisers directed at a single atomisation region may increase the area over which liquid aerosol-forming substrate is atomised in the atomisation region.

The plurality of surface acoustic wave atomisers enable surface acoustic waves to be directed at the atomisation region from different directions. The plurality of surface acoustic wave atomisers may comprise a first surface acoustic wave atomiser configured to generate surface acoustic waves in a first direction, and a second surface acoustic wave atomiser configured to generate surface acoustic waves in a second direction, the second direction being different to the first direction. In particular, providing a plurality of surface acoustic wave atomisers configured to direct surface acoustic waves at a single atomisation region, from different directions, may increase the area of the atomisation region to which surface acoustic waves are delivered. Advantageously, providing a plurality of surface acoustic wave atomisers directed at a single atomisation region from different directions may help to prevent liquid aerosol-forming substrate being supplied to an area of the atomisation region that does not receive surface acoustic waves.

In some embodiments, the plurality of surface acoustic wave atomisers may enable surface acoustic waves having different characteristics to be directed at the atomisation region. This may enable a single aerosol-generator, having a single liquid supply, to be optimised to generate aerosol from liquid aerosol-forming substrates having different characteristics.

The atomisation region is a common atomisation region for each of the plurality of surface acoustic wave atomisers, and is defined between the substrates of the plurality of surface acoustic wave atomisers. Each of the plurality of surface acoustic wave atomisers is arranged to direct surface acoustic waves in a direction towards the atomisation region.

Advantageously, providing a common atomisation region may reduce or minimise the size of each of the plurality of surface acoustic wave atomisers, and the overall size of the aerosol-generator. Advantageously, providing a common atomisation region may simplify the design and manufacture of an aerosol-generating device comprising the aerosol-generator. For example, providing a common atomisation region may facilitate a simple airflow path through the aerosol-generating device.

The aerosol-generator comprises a plurality of surface acoustic wave atomisers. The aerosol-generator may comprise any suitable number of surface acoustic wave atomisers. For example, the aerosol-generator may comprise two, three, four, five, six, seven eight or nine surface acoustic wave atomisers. The plurality of surface acoustic wave atomiser may comprise at least two surface acoustic wave atomisers. The plurality of surface acoustic wave atomisers may comprise at least three surface acoustic wave atomisers. The plurality of surface acoustic wave atomisers may consist of two surface acoustic wave atomisers. The plurality of surface acoustic wave atomisers may consist of three surface acoustic wave atomisers.

In some preferred embodiments, the aerosol-generator comprises an even number of surface acoustic wave atomisers. Where the aerosol-generator comprises an even number of surface acoustic wave atomisers, the surface acoustic wave atomisers may be provided in pairs of opposing surface acoustic wave atomisers. The pairs of opposing surface acoustic wave atomisers may comprise a first surface acoustic wave atomiser arranged to direct surface acoustic waves in a first direction towards the atomisation region, and a second surface acoustic wave atomiser arranged to direct surface acoustic waves in a second direction towards the atomisation region, the second direction being parallel and opposite to the first direction.

The following preferred and optional features of the surface acoustic wave atomiser may be applied to surface acoustic wave atomisers to the present disclosure.

Each of the plurality of surface acoustic wave atomisers comprises: a substrate comprising an active surface; and at least one transducer positioned on the active surface of the substrate for generating surface acoustic waves on the active surface of the substrate.

The substrate is formed from a substrate material. The substrate may be a piezoelectric material. The substrate may comprise a crystalline material. The substrate material may comprise a monocrystalline material. The substrate material may comprise a polycrystalline material. The substrate material may comprise at least one of quartz, a ceramic, barium titanate ($BaTiO_3$), and lithium niobate ($LiNbO_3$). The ceramic may comprise lead zirconate titanate (PZT). The ceramic may include doping materials such as Ni, Bi, La, Nd or Nb ions. The substrate material may be polarised. The substrate material may be unpolarised. The substrate material may comprise both polarised and unpolarised materials.

In some embodiments, the substrate material may comprise a non-crystalline base material. The non-crystalline base material may comprise any material onto which a piezoelectric material can be deposited. The non-crystalline base material may comprise a polymeric material. The non-crystalline base material may comprise a flexible or bendable material, such as a flexible film. The flexible or bendable non-crystalline base material may be formed from any suitable material, such as a plastics material. Nanocrystals or microcrystals of a piezoelectric material may be deposited or otherwise immobilized on the non-crystalline base material. The nanocrystals or microcrystals of a piezoelectric material may comprise any materials which exhibit piezoelectric properties. For example, the piezoelectric material may comprise one or more of lead zirconate Titanate (PZT), aluminium nitride (AlN), zinc oxide (ZnO), barium titanate ($BaTiO_3$), and lithium niobate ($LiNbO_3$). For example, the non-crystalline base material may comprise nanocrystals or microcrystals of zinc oxide (ZnO). In some embodiments, a flexible film of piezoelectric material may be deposited on the non-crystalline base material. In some embodiments, a flexible film of a monocrystalline piezoelectric material may be deposited on the non-crystalline base material. For example, the piezoelectric material may comprise polyvinylidene difluoride (PVDF). The substrate material may comprise a flexible film of a non-crystalline base material and a flexible film of polyvinylidene difluoride (PVDF) deposited on the non-crystalline base material. The flexible film of polyvinylidene difluoride (PVDF) may be a monocrystalline.

Advantageously, providing the substrate material with a non-crystalline base material, and particularly a flexible or bendable non-crystalline base material, may enable the substrate to be formed in a curved or a bent shape.

The substrate may comprise a surface treatment. The surface treatment may be applied to the active surface of the substrate. The surface treatment may comprise a coating. The coating may comprise a hydrophobic material. The coating may comprise a hydrophilic material. The coating may comprise an oleophobic material. The coating may comprise an oleophilic material.

In some preferred embodiments, each one of the plurality of surface acoustic wave atomisers may comprise the same substrate material. In some embodiments, at least one of the plurality of surface acoustic wave atomisers comprises a different substrate material to another one of the plurality of surface acoustic wave atomisers.

The substrate may have any suitable shape. In some embodiments, at least one of the plurality of surface acoustic wave atomisers comprises a substrate having a different shape to the substrate of another one of the plurality of acoustic wave atomisers. In some preferred embodiments, each of the substrates has the same shape.

The substrate may have a planar shape. In other words, the substrate may extend generally in one plane. In some embodiments, at least one of the plurality of surface acoustic wave atomisers comprises a substrate having a planar shape. In some preferred embodiments, each of the substrates has a planar shape.

The substrate may have a non-planar shape. In other words, the substrate may have sections extending in different planes. In some embodiments, the substrate may have a curved shape. In some embodiments, the substrate may have a first section extending in a first plane, and a second section extending in a second plane, the second plane being non-parallel with the first plane.

In some embodiments, at least one of the surface acoustic wave atomisers comprises a substrate having a planar shape, and at least one of the surface acoustic wave atomisers comprises a substrate having a non-planar shape. In some embodiments, each of the surface acoustic wave atomisers comprises a substrate having a planar shape. In some embodiments, each of the surface acoustic wave atomisers comprises a substrate having a non-planar shape.

The substrate may have a cylindrical shape or a polyhedral shape. The substrate may have a cylindrical shape, an elliptical cylindrical shape, a cuboidal shape, a prismatic shape, a triangular prismatic shape, a trapezoidal prismatic shape, or an isosceles trapezoidal prismatic shape. In some preferred embodiments, each of the substrates have the shape of an isosceles trapezoidal prism.

The substrate comprises an active surface on which surface acoustic waves are generated. The active surface may be a planar surface. The active surface may be a non-planar surface. In some embodiments, all of the active surfaces of the substrates of the plurality of surface acoustic wave atomisers are planar active surfaces. In some embodiments, all of the active surfaces of the substrates of the plurality of surface acoustic wave atomisers are non-planar active surfaces. In some embodiments, some of the active surfaces of the substrates of the plurality of surface acoustic wave atomisers are planar active surfaces, and some of the active surfaces of the substrates of the plurality of surface acoustic wave atomisers are non-planar active surfaces.

The active surface may have any suitable shape. The active surface may have a circular shape, an elliptical shape, or the shape of any suitable polygon. The active surface may have a triangular shape, a square shape, a rectangular shape, a pentagonal shape, a hexagonal shape or a trapezoidal shape. In some preferred embodiments, the active surface has the shape of an isosceles trapezoid.

In some preferred embodiments, the active surfaces of each substrate of the plurality of surface acoustic wave atomisers have the same shape. In some embodiments, at least one of the surface acoustic wave atomisers comprises a substrate having an active surface having a shape that is different to the shape of the active surface of the substrate of at least one of the other surface acoustic wave atomisers.

Where the substrate comprises a crystalline material, the active surface of the substrate may be defined by a lattice plane of the crystalline material.

The substrates of the plurality of surface acoustic wave atomisers may be arranged in any suitable arrangement.

In some embodiments, the substrates of the plurality of surface acoustic wave atomisers may be spaced apart. In other words, a gap or space may be provided between adjacent surface acoustic wave atomisers.

Preferably, the substrates of the plurality of surface acoustic wave atomisers abut each other. In other words, preferably the substrates of the plurality of surface acoustic wave atomisers are in contact with each other. The plurality of surface acoustic wave atomisers may be in direct contact with each other. The plurality of surface acoustic wave atomisers may be in indirect contact with each other. Where the substrates of the plurality of surface acoustic wave atomisers abut each other, the substrates may be connected together. For example, the substrates may be fixed together. The substrates may be fixed together by an adhesive. Where adjacent substrates are fixed together by an adhesive, the adjacent substrates are indirectly in contact with each other, via a layer of adhesive between the substrates.

The substrates may be arranged to define an opening. Preferably, the substrates of the plurality of surface acoustic wave atomisers abut each other to define an opening bounded by the substrates. Preferably, the opening bounded by the substrates is at the atomisation region. In some embodiments, the opening bounded by the substrates may form the atomisation region.

In some embodiments in which each of the substrates has a planar active surface, the active surfaces of the substrates of the plurality of surface acoustic wave atomisers are positioned in a common plane. Advantageously, positioning the active surfaces of the substrates of the plurality of surface acoustic wave atomisers in a common plane may simplify manufacture of the aerosol-generator.

In some embodiments in which each of the substrates has a planar active surface, the active surfaces of the substrates of the plurality of surface acoustic wave atomisers are positioned in a non-coplanar arrangement with respect to each other. Advantageously, positioning the active surfaces of the substrates of the plurality of surface acoustic wave atomisers in a non-coplanar relationship with each other may enable the aerosol-generator to be compact. Advantageously, positioning the active surfaces of the substrates of the plurality of surface acoustic wave atomisers in a non-coplanar relationship with each other may provide a space or volume in between the substrates to accommodate a liquid supply, or provide for an airflow passageway. Advantageously, positioning the active surfaces of the substrates of the plurality of surface acoustic wave atomisers in a non-coplanar relationship with each other may enable airflow over the active surfaces to be controlled.

In some preferred embodiments in which each of the substrates has a planar active surface, the substrates of the plurality of surface acoustic wave atomisers are arranged to form a polyhedral shape. Advantageously, arranging the substrates of the plurality of surface acoustic wave atomisers in a polyhedral shape may enable the aerosol-generator to be compact.

In some preferred embodiments in which the substrates of the plurality of surface acoustic wave atomisers abut each other to define an opening bounded by the substrates, the opening bounded by the substrates forming the atomisation region, the plurality of surface acoustic wave atomisers comprises at least three surface acoustic wave atomisers. In some preferred embodiments in which the plurality of surface acoustic wave atomisers comprises at least three surface acoustic wave atomisers, each of the substrates may have an isosceles trapezoidal prismatic shape.

In some particularly preferred embodiments in which the plurality of surface acoustic wave atomisers comprises at least three surface acoustic wave atomisers, and each of the substrates has an isosceles trapezoidal prismatic shape, the active surfaces may have an isosceles trapezoidal shape, and the shortest edges of each of the planar isosceles trapezoidal shapes may together define the opening. In these particularly preferred embodiments, the active surfaces of the substrates of the plurality of surface acoustic wave atomisers may be arranged in a non-coplanar arrangement, such that the plurality of surface acoustic wave atomisers form a truncated pyramidal shape. Where the plurality of surface acoustic wave atomisers form a truncated pyramidal shape, the atomisation region may be positioned at the narrow end of the truncated pyramid. Where the plurality of surface acoustic wave atomisers form a truncated pyramidal shape, and the substrates are arranged to form an opening, the opening may be positioned at the narrow end of the truncated pyramid.

Advantageously, arranging the substrates of the plurality of surface acoustic wave atomisers in a substantially truncated pyramidal shape may enable the aerosol-generator to be compact.

In some embodiments, the substrates may comprise a material that is flexible or bendable. In these embodiments, the substrate may be formed into a bent or a curved shape. Where the substrates are formed into a bent or a curved shape, the plurality of surface acoustic wave atomisers may be arranged in the form of a cylinder or a cone.

In embodiments in which the substrates of the plurality of surface acoustic wave atomisers abut each other to define an opening bounded by the substrates, the opening bounded by the substrates forming the atomisation region, an edge portion of each of the substrates may partially define the opening. Each edge portion may have any suitable profile. For example, each edge portion may have one of a square profile, a rounded profile, a triangular profile, or a bevelled profile. Advantageously, providing each edge portion with a rounded, triangular or bevelled profile may facilitate delivery of the liquid aerosol-forming substrate into the atomisation region.

Preferably, each of the at least one transducers is arranged for generating surface acoustic waves in a direction towards the atomisation region. Where the substrates are arranged to define an opening, preferably, each of the at least one transducers is arranged for generating surface acoustic waves in a direction towards the opening.

The at least one transducer may comprise an interdigital transducer comprising a plurality of electrodes. The at least one transducer may comprise an interdigital transducer comprising an array of interleaved electrodes. Preferably, the plurality of electrodes are substantially parallel with each other. Preferably, the interdigital transducer comprises a first array of electrodes and a second array of electrodes interleaved with the first array of electrodes. Preferably, the first array of electrodes is substantially parallel with the second array of electrodes.

The transducer may be configured to generate surface acoustic waves having a substantially linear wavefront. In embodiments in which the transducer is an interdigital transducer comprising a plurality of electrodes, each electrode may be substantially linear.

The transducer may be configured to generate surface acoustic waves having a curved wavefront. In embodiments in which the transducer is an interdigital transducer comprising a plurality of electrodes, each electrode may be curved. The transducer may be configured to generate surface acoustic waves having a convex wavefront. Preferably, the transducer may be configured to generate surface acoustic waves having a concave wavefront. Advantageously, a concave wavefront may provide a focusing effect. In other words, a concave wavefront may focus the generated surface acoustic waves towards an atomisation region that is smaller than the transducer. Advantageously, focusing the generated surface acoustic waves may increase the rate at which energy is delivered to a liquid aerosol-forming substrate in the atomisation region.

The array of interleaved electrodes of the interdigital transducer may have a symmetrical shape comprising a line of symmetry extending in a direction.

Where the substrate comprises a crystalline material, and the active surface of the substrate may be defined by a lattice plane of the crystalline material, the direction of the line of symmetry of the array of interleaved electrodes may be aligned with a lattice vector of the lattice plane. Advantageously, aligning the directions of the line of symmetry of the array of interleaved electrodes with lattice vectors of the lattice plane of the substrate may facilitate the generation of an acoustic wavefront having a desired shape. The desired shape may be a symmetrical shape.

The at least one transducer may be a unidirectional transducer or a bidirectional transducer. In some preferred embodiments, the at least one transducer is a single-phase unidirectional transducer.

The at least one transducer may be a single transducer. The at least one transducer may be a plurality of transducers. In embodiments in which the surface acoustic wave atomiser comprises a plurality of transducers, preferably each transducer is arranged on the active surface of the substrate so that surface acoustic waves generated by the transducer travel towards the atomisation region.

Each surface acoustic wave atomiser may comprise any suitable number of transducers. For example, the surface acoustic wave atomiser may comprise one, two, three or four transducers. Preferably, each surface acoustic wave atomiser comprises the same number of transducers. The surface acoustic wave atomisers may comprise different numbers of transducers.

Where a surface acoustic wave atomiser comprises a plurality of transducers, preferably each of the plurality of transducers is the same. However, in some embodiments, a surface acoustic wave atomiser comprising a plurality of transducers may comprise transducers that are different.

In embodiments in which the surface acoustic wave atomiser comprises a plurality of transducers, each transducer may comprise an impedance matching component. Providing an impedance matching component may be advantageous when the load impedance of the transducers differ significantly relative to each other. Providing an impedance matching component may be advantageous when the load impedance of the transducers differ significantly relative to the source impedance of a controller which generates a drive signal provided to the transducers.

In embodiments in which the surface acoustic wave atomiser comprises a plurality of transducers, the transducers may be connected in series. In embodiments in which the surface acoustic wave atomiser comprises a plurality of transducers, the transducers may be connected in parallel.

The atomisation region is defined between the substrates of the plurality of surface acoustic wave atomisers. Each of the plurality of surface acoustic wave atomisers is arranged to direct surface acoustic waves in a direction towards the atomisation region. Where the substrates are arranged to define an opening, the opening may be arranged in the atomisation region. In some embodiments, the opening may define the atomisation region. Preferably, each of the at least one transducers is arranged for generating surface acoustic waves in a direction towards the opening.

The aerosol-generator comprises a supply element. The supply element is arranged to supply a liquid aerosol-forming substrate to the atomisation region. Where the substrates are arranged to define an opening, the supply element may be arranged at the opening.

The supply element may comprise any suitable type of supply element that is capable of supplying a liquid aerosol-forming substrate to the atomisation region.

The supply element may comprise at least one of a capillary channel or a capillary wick. In some preferred embodiments, the supply element comprises a capillary wick extending into the atomisation region.

The supply element may comprise a channel extending at least partially through the substrate of at least one of the plurality of surface acoustic wave atomisers. The channel may extend between an inlet on a passive surface of the substrate of at least one of the plurality of surface acoustic wave atomisers and an outlet at the atomisation region. In these embodiments, the active surface of the substrate may be curved, bevelled or angled at or around the atomisation region in a direction towards the passive surface. Advantageously, curving or angling the active surface towards the passive surface at or around the atomisation region may facilitate delivery of surface acoustic waves to the outlet.

In some preferred embodiments, each of the substrates comprises a passive surface opposite the active surface. In these embodiments, the supply element may comprise a groove formed in the passive surface of at least one of the substrates, the groove having an end in fluid communication with the atomisation region.

In some particularly preferred embodiments, the plurality of surface acoustic wave atomisers comprises a first surface acoustic wave atomiser comprising a first substrate and a second surface acoustic wave atomiser comprising a second substrate. In these preferred embodiments, the first substrate .channel in fluid communication with the atomisation region. In these particularly preferred embodiments, the first and second grooves may have complimentary shapes.

The supply element may comprise a flow control element arranged to control a flow of the liquid aerosol-forming substrate to the atomisation region. In embodiments in which the supply element comprises a channel, preferably the first flow control element is arranged to control a flow of the aerosol-forming substrate through the inlet of the channel.

The flow control element may comprise at least one passive element. The at least one passive element may comprise at least one of a capillary tube and a capillary wick.

The flow control element may comprise at least one active element. The at least one active element may comprise at least one of a micro pump, a syringe pump, a piston pump, and an electroosmotic pump.

Preferably, the controller is configured to provide a flow signal to the flow control element to enable a flow of the liquid aerosol-forming substrate to the common atomisation region. The controller may be configured to provide a stop signal to the control element to disable the flow of the first liquid aerosol-forming substrate.

The aerosol-generator may comprise a controller. Preferably, the controller is configured to provide a drive signal to the at least one transducer of each of the plurality of surface acoustic wave atomisers for generating surface acoustic waves on the active surfaces of the substrates. In order to provide a drive signal to the at least one transducer of each of the plurality of surface acoustic wave atomisers, the controller may comprise a signal generator configured to generate a drive signal and an amplifier configured to amplify the drive signal generated by the signal generator, such that an amplified drive signal can be provided to the at least one transducer.

In embodiments in which the surface acoustic wave atomiser comprises a plurality of transducers connected in series, and the controller comprises an amplifier and a signal generator, a drive signal generated by the signal generator may be amplified by the amplifier and provided to each of the plurality of transducers connected in series.

In embodiments in which the surface acoustic wave atomiser comprises a plurality of transducers connected in parallel, and the controller comprises an amplifier and a signal generator, a drive signal generated by the signal generator may be amplified by the amplifier and provided to each of the plurality of transducers connected in parallel.

The controller may be configured to provide the same drive signal to the at least one transducer of each of the plurality of surface acoustic wave atomisers. The controller may be configured to provide different drive signals to the at least one transducer of each of the plurality of surface acoustic wave atomisers. Advantageously, providing different drive signals to the at least one transducer of each of the plurality of surface acoustic wave atomisers may enable the aerosol-generator to vary the characteristics of the aerosol generated by the generator, and may enable the aerosol-generator to be optimised to vaporise different liquid aerosol-forming substrates.

When the controller is configured to provide the same drive signal to the at least one transducer of each of the plurality of surface acoustic wave atomisers, a splitter may be arranged between the controller and the at least one transducer of each of the plurality of surface acoustic wave atomisers in order to split the drive signal into a plurality of channels, each channel being connected to only one of the at least one transducer. Using a splitter may be beneficial in that the output of the splitter to each of the plurality of channels is independent from the load characteristics of each channel. This may be advantageous in that, even if one of the at least one transducer is dysfunctional, the provision of the drive signal to the remaining transducers can be kept under the same conditions.

When the controller comprises a signal generator and an amplifier, a splitter may be arranged between the amplifier and the at least one transducer of each of the plurality of surface acoustic wave atomisers. This may allow for the an amplified signal to be provided to each of the at least one transducer even in the embodiment in which the controller provides the same drive signal.

The controller may be configured to provide a drive signal to the at least one transducer of each of the plurality of surface acoustic wave atomisers simultaneously. Advantageously, providing a drive signal to the at least one transducer of each of the plurality of surface acoustic wave atomisers simultaneously may provide optimised atomisation of liquid aerosol-forming substrate at the atomisation region and may enable straightforward programming of the controller.

The controller may be configured to provide a drive signal to the at least one transducer of each of the plurality of surface acoustic wave atomisers sequentially. In other words, the controller may be configured to provide a drive signal to the at least one transducer of each of the plurality of surface acoustic wave atomisers one after the other. Advantageously, providing a drive signal to the at least one transducer of each of the plurality of surface acoustic wave atomisers sequentially may enable the aerosol-generator to vary the characteristics of the aerosol generated by the generator over time.

When the controller is configured to provide a drive signal to the at least one transducer of each of the plurality of surface acoustic wave atomisers sequentially, the controller may comprise a switch configured to select the transducer of the at least one transducer to which the drive signal is provided. The controller may comprise a signal source. The signal source may be configured to determine the frequency of the drive signal. The signal source may determine the frequency of the drive signal in function of the position of the switch. Put another way, the frequency of the drive signal can be adapted to the characteristics of the transducer to which the drive signal is provided.

The switch may be configured to vary its position in less than a millisecond. This allows for a sequential operation of the at least one transducer even within a short time interval, which may enable the generation of an aerosol with more specific characteristics over a given period of time.

The controller may be configured to provide a drive signal to the at least one transducer of each of the plurality of surface acoustic wave atomisers individually. In other words, the controller may be configured to selectively provide a drive signal to the at least one transducer of each of the plurality of surface acoustic wave atomisers. Advantageously, providing a drive signal to the at least one transducer of each of the plurality of surface acoustic wave atomisers individually may enable the aerosol-generator to be used with different liquid aerosol-forming substrates, wherein each surface acoustic wave atomiser is optimised to vaporise a different liquid aerosol-forming substrate.

In some embodiments, the aerosol-generator comprises a plurality of controllers. In some embodiments, each surface acoustic wave atomiser comprises a controller configured to provide a drive signal to the at least one transducer.

In the embodiment in which the aerosol-generator comprises a plurality of controllers, each controller may be configured to provide a drive signal to only one of the at least one transducer. This configuration may be useful for aerosol-generators in which each of the at least one transducer is different with respect to each other.

In embodiments in which the surface acoustic wave atomiser comprises a plurality of transducers, such as a plurality of transducers connected in series or in parallel, the transducers may be arranged to define a resonating system with characteristic frequencies. The resonating system may be arranged to define resonance frequencies substantially equal to the resonance frequencies of each of the at least one transducer. In the latter embodiment, the controller may be configured to provide a drive signal having a frequency substantially equal to the resonance frequency of one of the at least one transducer. It has been found out that, when the drive signal has such frequency, the drive signal is mostly transferred only to the transducer whose resonance frequency substantially coincides with the frequency of the drive signal. Such configuration may allow for a sequential activation of the at least one transducer without a need for dedicated components, such as a switch. Put another way, one of the at least one transducer may be selectively activated by selecting the appropriate frequency for the drive signal.

In embodiments in which the aerosol-generator comprises a flow control element, and the aerosol-generator comprises at least one controller, preferably, the controller is configured to provide a flow signal to the flow control element to enable a flow of the liquid aerosol-forming substrate to the atomisation region. Preferably, the controller is configured to provide a stop signal to the control element to disable the flow of the liquid aerosol-forming substrate. Preferably, the controller is configured to provide the drive signal to the at least one transducer of one or more of the surface acoustic wave atomisers only when the controller provides the flow signal to the flow control element.

At least one of the plurality of surface acoustic wave atomisers may comprise at least one reflector. In some embodiments, each of the plurality of surface acoustic wave atomisers may comprise at least one reflector. Preferably, the at least one reflector is positioned on the active surface of the substrate. Preferably, the at least one reflector is arranged to reflect surface acoustic waves generated by the at least one transducer. Preferably, the at least one reflector is arranged to reflect surface acoustic waves generated by the transducer towards the atomisation region. Advantageously, a reflector arranged to reflect surface acoustic waves towards the atomisation region may increase or maximise the efficiency of the surface acoustic wave atomiser.

The at least one reflector may comprise one or more electrodes.

The at least one reflector may comprise one or more portions of metal positioned on the active surface of the substrate. Each portion of metal may have a linear shape. Each portion of metal may have a curved shape. The at least one reflector may comprise a plurality of portions of metal. The plurality of portions of metal may be arranged in a pattern on the active surface of the substrate. Preferably, each portion of metal is substantially parallel to the adjacent portions of metal forming the at least one reflector.

A portion of the substrate may form at least part of the at least one reflector. The substrate may define at least one protrusion, wherein the at least one protrusion forms at least part of the at least one reflector. The substrate may define at least one recess, wherein the at least one recess forms at least part of the at least one reflector.

The atomisation region may be positioned between the at least one transducer and the at least one reflector.

The at least one reflector may be a single reflector. The at least one reflector may be a plurality of reflectors.

In embodiments in which at least one of the plurality of surface acoustic wave atomisers comprises a plurality of transducers, the at least one reflector may be a plurality of reflectors. Each of the transducers may be positioned opposite one of the reflectors so that the atomisation region is positioned between the transducer and the corresponding reflector.

At least one of the plurality of surface acoustic wave atomisers may comprise at least one absorber. Preferably, the at least one absorber is positioned on the active surface of the substrate of the surface acoustic wave atomiser. Preferably, the at least one absorber is arranged to absorb surface acoustic waves generated by the at least one transducer. A portion of the substrate may form at least part of the at least one absorber. The substrate may define at least one protrusion, wherein the at least one protrusion forms at least part of the at least one absorber. The substrate may define at least one recess, wherein the at least one recess forms at least part of the at least one absorber.

The at least one absorber may comprise a material having one or more of a low density, and a high viscosity, such as polydimethylsiloxane (PDMS). Advantageously, providing an absorber with a material having one or more of a low density, and a high viscosity may provide the absorber with a relatively high acoustic absorption coefficient. Preferably, the absorber comprises a material in which the speed of sound is relatively low. The absorber may comprise a porous material. In some preferred embodiments, the absorber comprises polydimethylsiloxane (PDMS).

A portion of the substrate may form at least part of the at least one absorber. The substrate may define at least one protrusion, wherein the at least one protrusion forms at least part of the at least one absorber. The substrate may define at least one recess, wherein the at least one recess forms at least part of the at least one absorber.

According to the present disclosure there is also provided an aerosol-generating device comprising an aerosol-generator according the present disclosure. The aerosol-generating device may comprise a controller for controlling the at least one transducer of each surface acoustic wave atomiser. The aerosol-generating device may comprise a power supply. The aerosol-generating device may comprise a liquid storage portion for receiving a liquid aerosol-forming substrate. The supply element of the aerosol-generator may be arranged to supply liquid aerosol-forming substrate from the liquid storage portion to the atomisation region.

The at least one liquid storage portion may be reusable. In other words, the at least one liquid storage portion may be refillable by a user to replenish a liquid aerosol-forming substrate in the at least one liquid storage portion. The at least one liquid storage portion may comprise a refill aperture for inserting a liquid aerosol-forming substrate into the liquid storage portion. The at least one liquid storage portion may comprise a refill valve between the refill aperture and the at least one liquid storage portion. Advantageously, the refill valve may allow a liquid aerosol-forming substrate to flow through the refill aperture into the at least one liquid storage portion. Advantageously, the refill valve may prevent a liquid aerosol-forming substrate from flowing out of the at least one liquid storage portion through the refill aperture.

The at least one liquid storage portion may be replaceable. The at least one liquid storage portion may be removable from the aerosol-generating device. The aerosol-generating device may comprise a cartridge, wherein the cartridge is removable from the aerosol-generating device, and wherein the cartridge comprises the at least one liquid storage portion.

The aerosol-generating device may comprise a liquid aerosol-forming substrate contained within the at least one liquid storage portion.

The liquid aerosol-forming substrate may comprise nicotine. The nicotine containing liquid aerosol-forming substrate may be a nicotine salt matrix. The liquid aerosol-forming substrate may comprise plant-based material. The liquid aerosol-forming substrate may comprise tobacco. The liquid aerosol-forming substrate may comprise homogenised tobacco material. The liquid aerosol-forming substrate may comprise a non-tobacco-containing material. The liquid aerosol-forming substrate may comprise homogenised plant-based material.

The liquid aerosol-forming substrate may comprise at least one aerosol-former. An aerosol-former is any suitable known compound or mixture of compounds that, in use, facilitates formation of a dense and stable aerosol. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Aerosol formers may be polyhydric alcohols or mixtures thereof, such as triethylene glycol, 1,3-butanediol and glycerine. The liquid aerosol-forming substrate may comprise other additives and ingredients, such as flavourants.

The liquid aerosol-forming substrate may comprise water.

The liquid aerosol-forming substrate may comprise nicotine and at least one aerosol former. The aerosol former may comprise glycerine. The aerosol-former may comprise propylene glycol. The aerosol former may comprise both glycerine and propylene glycol. The liquid aerosol-forming substrate may have a nicotine concentration of between about 0.1 percent and about 10 percent.

In embodiments in which the inlet of the supply element comprises a plurality of inlets, the at least one liquid storage portion may comprise a first liquid storage portion and a second liquid storage portion. The first liquid storage portion is for receiving a first liquid aerosol-forming substrate, wherein the first liquid storage portion is in fluid communication with a first inlet of the plurality of inlets. The second liquid storage portion is for receiving a second liquid aerosol-forming substrate, wherein the second liquid storage portion is in fluid communication with a second inlet of the plurality of inlets.

The aerosol-generating device may comprise a flow control element arranged to control a flow rate of liquid aerosol-forming substrate from the at least one liquid storage portion to the channel of the supply element.

The flow control element may comprise at least one passive element. The at least one passive element may comprise at least one of a capillary tube and a capillary wick. The at least one passive element may comprise a capillary tube. The at least one passive element may comprise a capillary wick.

The flow control element may comprise at least one active element. The at least one active element may comprise a pump. The at least one active element may comprise at least one of a micro pump, a syringe pump, a piston pump, and an electroosmotic pump. Preferably, the controller is arranged to provide a control signal to the at least one active element to control a flow rate of liquid aerosol-forming substrate from the at least one liquid storage portion to the channel of the supply element.

The controller may comprise electric circuitry connected to the power supply and the aerosol-generator. The controller may comprise electric circuitry connected to the power supply and the at least one transducer of each of the plurality of surface acoustic wave atomisers. Where the aerosol-generator comprises at least one controller, the controller of the aerosol-generating device may be connected to the at least one controller of the aerosol-generator. The electric circuitry may comprise a microprocessor. The microprocessor may be a programmable microprocessor, a microcontroller, or an application specific integrated chip (ASIC) or other electronic circuitry capable of providing control. The electric circuitry may comprise further electronic components. The electric circuitry may be configured to regulate a supply of power from the power supply to the aerosol-generator. The electric circuitry may be configured to regulate a supply of power from the power supply to the at least one transducer of each of the plurality of surface acoustic wave atomisers. The controller may be configured to supply power continuously to the aerosol-generator following activation of the aerosol-generative device. The controller may be configured to supply power intermittently to the aerosol-generator. The controller may be configured to supply power to the aerosol-generator on a puff-by-puff basis.

Preferably, the controller and the power supply are configured to provide an alternating voltage to the aerosol-generator. Preferably, the controller and the power supply are configured to provide an alternating voltage to the at least one transducer of each of the plurality of surface acoustic wave atomisers. Preferably, the alternating voltage is a radio frequency alternating voltage. Preferably, the alternating voltage has a frequency of at least about 20 megahertz. Preferably, the alternating voltage has a frequency of between about 20 megahertz and about 100 megahertz, more preferably between about 20 megahertz and about 80 megahertz. Advantageously, an alternating voltage within these ranges may provide at least one of a desired rate of aerosol generating and a desired droplet size.

The power supply may be any suitable type of power supply. The power supply may be a DC power supply. In some preferred embodiments, the power supply is a battery, such as a rechargeable lithium ion battery. The power supply may be another form of charge storage device, such as a capacitor. The power supply may require recharging. The power supply may have a capacity that allows for the storage of enough energy for one or more uses of the device. For example, the power supply may have sufficient capacity to allow for the continuous generation of aerosol for a period of around six minutes, corresponding to the typical time taken to smoke a conventional cigarette, or for a period that is a multiple of six minutes. In another example, the power supply may have sufficient capacity to allow for a predetermined number of uses of the device or discrete activations. In one embodiment, the power supply is a DC power supply having a DC supply voltage in the range of about 2.5 Volts to about 4.5 Volts and a DC supply current in the range of about 1 Amp to about 10 Amps (corresponding to a DC power supply in the range of about 2.5 Watts to about 45 Watts).

The aerosol-generating device may advantageously comprise a DC/AC inverter, which may comprise a Class-C, Class-D or Class-E power amplifier. The DC/AC inverter may be arranged between the power supply and the aerosol-generator. The DC/AC inverter may be arranged between the power supply and the at least one transducer of each of the plurality of surface acoustic wave atomisers.

The aerosol-generating device may further comprise a DC/DC converter between the power supply and the DC/AC inverter.

The aerosol-generating device may comprise a temperature sensor arranged at or around the atomisation region of the aerosol-generator. The controller of the aerosol-generating device may be configured to control the power supplied to the aerosol-generator based on the temperature of the atomisation region sensed by the temperature sensor.

The aerosol-generating device may comprise a liquid detection sensor at or around the atomisation region of the aerosol-generator. The controller of the aerosol-generating device may be configured to supply power to the aerosol-generator when liquid is detected at the atomisation region by the liquid detection sensor.

The aerosol-generating device may comprise a puff detector, such as an airflow sensor or a pressure sensor. The puff detector may be arranged in an airflow pathway of the aerosol-generating device. The controller of the aerosol-generating device may be configured to supply power to the aerosol-generator when a puff on the device is detected by the puff detector.

The aerosol-generating device may comprise a device housing. The device housing may be elongate. The device housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

The device housing may define an air inlet. The air inlet may be configured to enable ambient air to enter the device housing. The air inlet may be in fluid communication with the atomisation region of the aerosol generator. The device may comprise any suitable number of air inlets. The device may comprise a plurality of air inlets.

The device housing may comprise an air outlet. The air outlet may be configured to enable air to exit the device housing for delivery to a user. The air outlet may be in fluid communication with the atomisation region of the aerosol generator. The aerosol-generating device may comprise a mouthpiece. The mouthpiece may comprise the air outlet. The device may comprise any suitable number of air outlets. The device may comprise a plurality of air outlets.

In some preferred embodiments, the aerosol-generating device may comprise a device housing, wherein the aerosol-generator is positioned within the device housing. In some of these preferred embodiments, the device housing defines at least one air inlet positioned upstream of the atomisation region and at least one air outlet positioned downstream of the atomisation region.

Advantageously, providing an air inlet positioned upstream of the atomisation region and at least one air outlet positioned downstream of the atomisation region may ensure that airflow between the air inlet and the air outlet passes over the atomisation region, which may result in vapour generated by the aerosol-generator at the atomisation region being entrained in the airflow between the air inlet and the air outlet.

The aerosol-generator may be arranged within the device housing to define an airflow pathway extending between at least one of the plurality of substrates and a portion of the device housing. The aerosol-generator may be arranged within the device housing to define an airflow pathway extending between each of the plurality of substrates and a portion of the device housing.

Advantageously, defining an airflow pathway between a substrate and a portion of the device housing may facilitate control of airflow through the airflow pathway, enabling the dimensions of the airflow pathway to be closely controlled.

The aerosol-generator may be attached to a support by an attachment means. The attachment means may comprise a mechanical attachment. The mechanical attachment may comprise a mechanical clamp. The mechanical clamp may comprise a recess in the support into which the aerosol-generator can be snap-fitted. The mechanical attachment may comprise a spring clamping. The spring clamping may comprise a flat spring; it may also comprise a pogo pin. The attachment means may comprise an adhesive material, such as an adhesive tape or an adhesive glue.

The support may comprise the power supply. The support may comprise the controller. The support may comprise a splitter. The support may be a printed circuit board (PCB). The PCB may comprise the controller. The PCB may comprise the splitter.

When the controller comprises electric circuitry to connect the power supply and the aerosol-generator, and the controller is comprised in the support, a wire-bonding electrical connection may be provided between the electric circuitry of the support and the aerosol-generator. More particularly, the wire-bonding electrical connection may be provided between the control circuitry of a PCB and the aerosol-generator, when the support is a PCB. The provision of a wire-bonding electrical connection may be advantageous in that the resulting electrical connection may be stable. The wire-bonding electrical connection may be directly connected to the electric circuitry, for example by soldering, screwing or clamping.

When the controller comprises electric circuitry to connect the power supply and the aerosol-generator, the controller is comprised in the support, and the aerosol-generator is attached to the support by means of a spring clamping, the spring clamping may be configured to provide an electrical connection between the electric circuitry of the support and the aerosol-generator. The provision of an electrical connection by spring clamping may be useful for the support and the aerosol-generator to be easily detached from one another.

The support may be provided in the aerosol-generating device. More particularly, the support may be provided in the device housing. The device housing may comprise an electrically conducting piece configured to provide an electrical connection between the support and the aerosol-generator. More particularly, in the embodiment in which the support is a PCB, the PCB may comprise a contact pin configured to be arranged in electrical contact with the electrically conductive piece of the of the device housing. Likewise, the aerosol-generator may comprise a contact pin configured to be arranged in electrical contact with the electrically conductive piece of the device housing. The PCB may comprise a contact pin configured to be arranged in electrical contact with a contact pin of the aerosol-generator. In the embodiment in which the PCB comprises a contact pin configured to be arranged in electrical contact with a contact pin of the aerosol-generator, the electrical connection between the PCB and the aerosol-generator can be established without a need for an intermediate electrically conducting piece in the device housing. This may facilitate the assembly and exchange of the support and the aerosol-generator.

When the controller is a PCB which comprises electric circuitry to connect the power supply and the aerosol-generator, the contact pin of the PCB may be provided at the control circuitry. The contact pin of the aerosol-generator may be provided at the at least one transducer.

The invention will be further described, by way of example only, with reference to the accompanying drawings, in which.

Figure 9A:
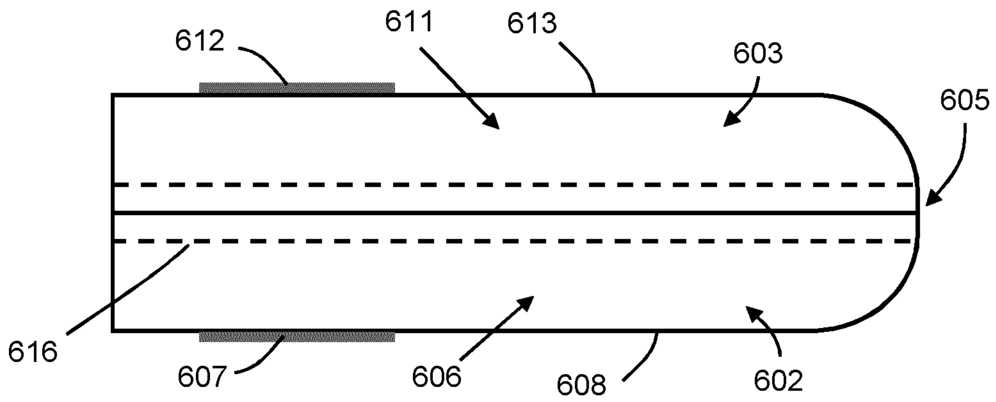
Figure 9B:
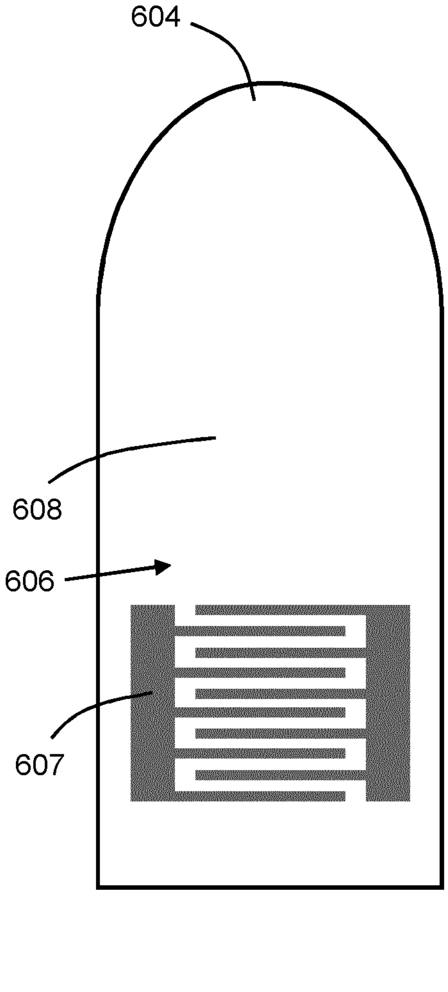

FIG. 9*a* shows a side view of an aerosol-generator according to a fourth embodiment of the present disclosure;

FIG. 9*b* shows a top view of a surface acoustic wave atomiser of the aerosol-generator of FIG. 9*a;*

Figure 9C:
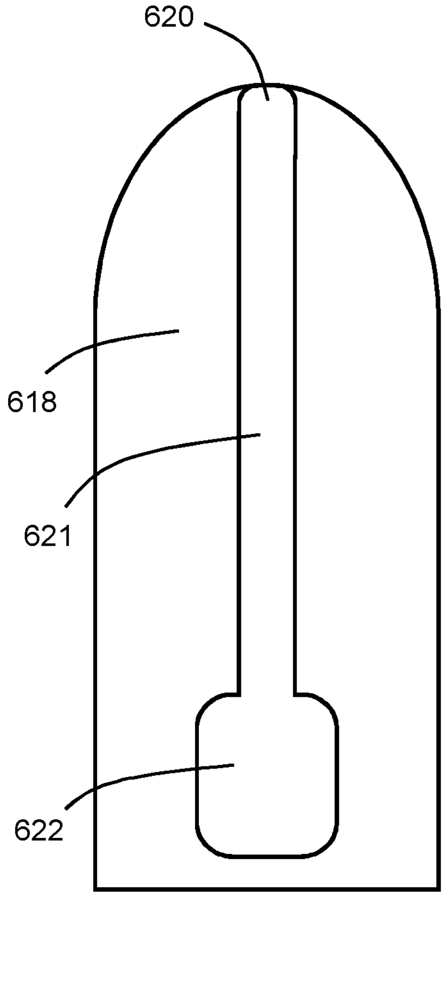

FIG. 9*c* shows a rear view of the surface acoustic wave atomiser of the aerosol-generator of FIG. 9*a;*

Figure 10A:
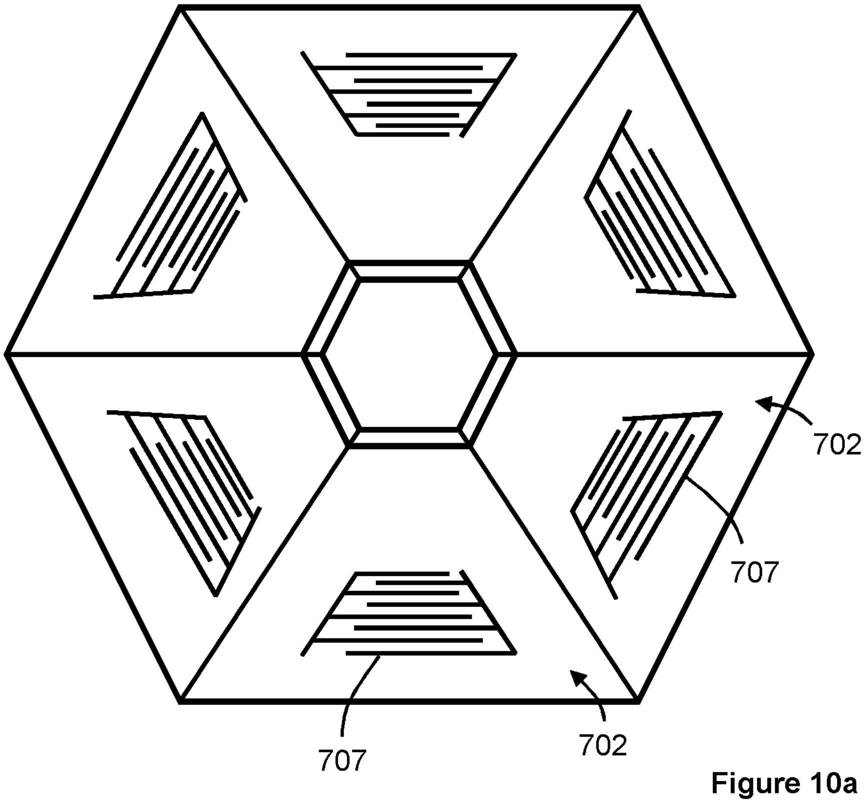
Figure 10B:
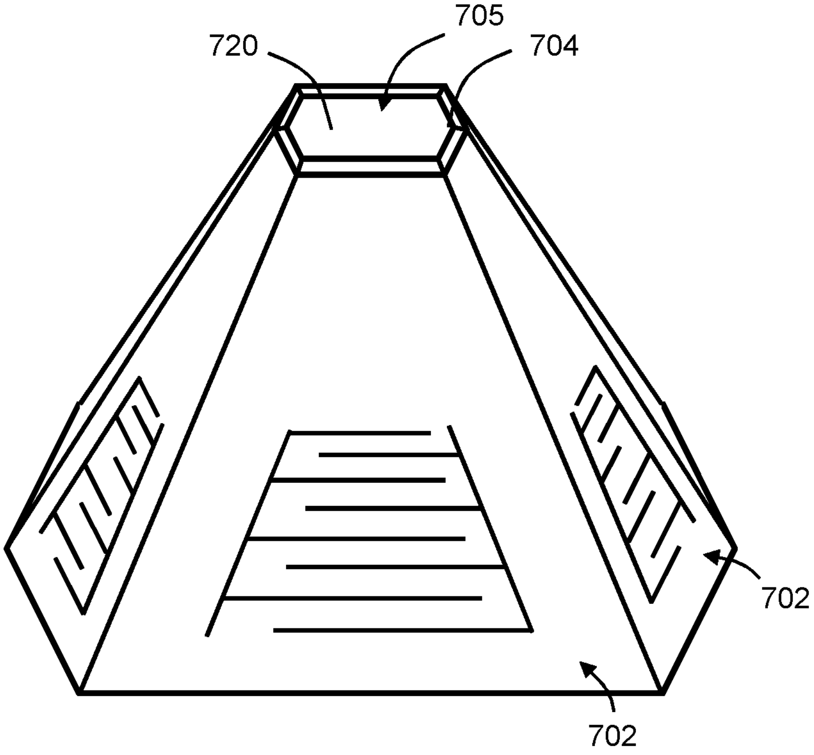

FIG. 10*a* shows a top view of an aerosol-generator according to a fifth embodiment of the present disclosure; and FIG. 10*b* shows a perspective view of the aerosol-generator of FIG. 10*a*.

Figure 1:
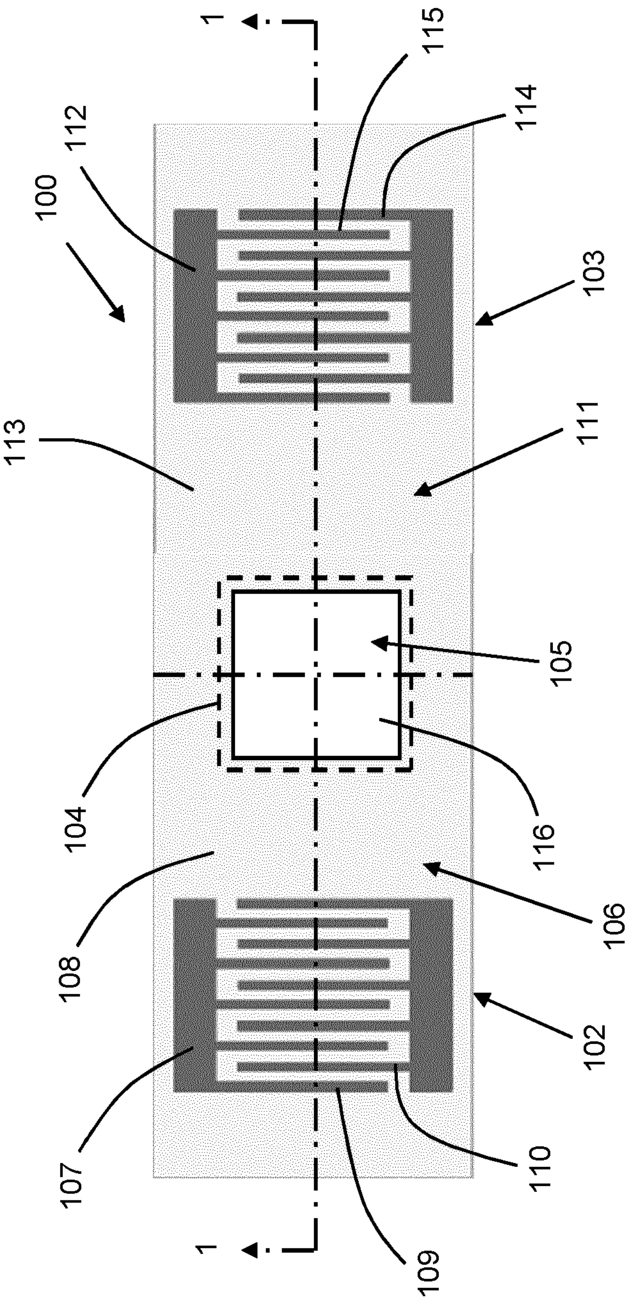
FIG. 1 shows a top view of an aerosol-generator according to a first embodiment of the present disclosure.
Figure 2:
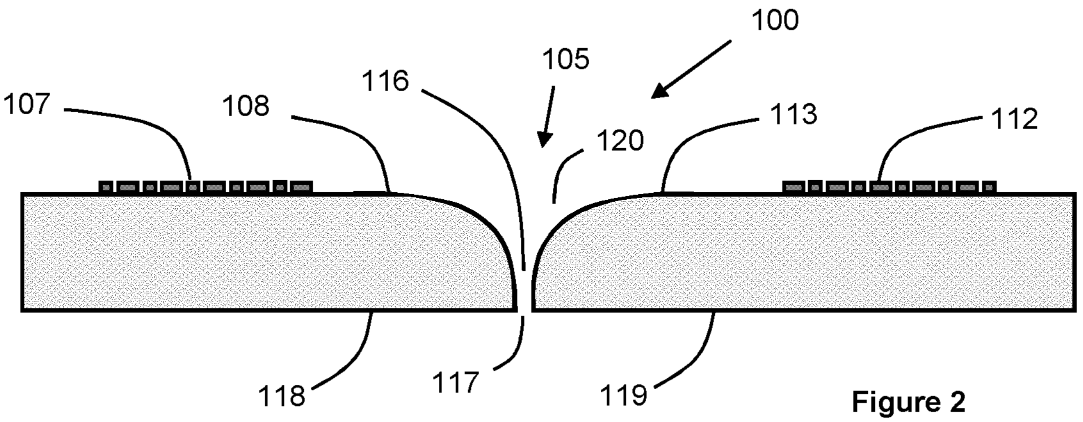
FIG. 2 shows a cross-sectional view of the aerosol-generator of FIG. 1 taken along line 1-1.
Figure 3:
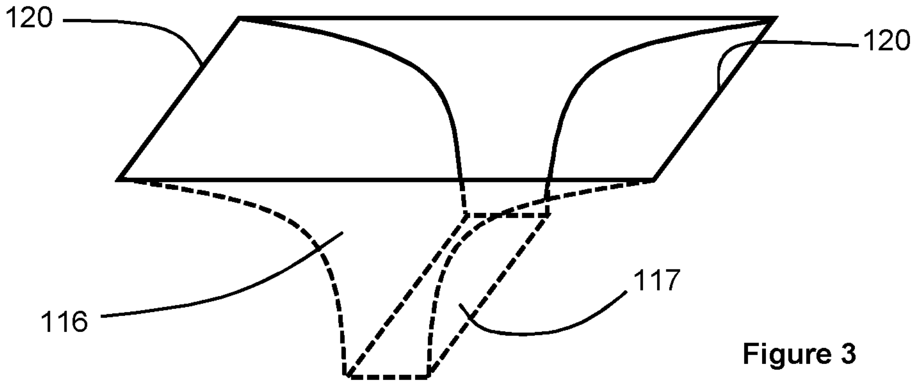
FIG. 3 shows a perspective view of the channel of the aerosol-generator of FIG. 1.

FIGS. 1, 2, and 3 show an aerosol-generator 100 according to a first embodiment of the present disclosure. The aerosol-generator 100 comprises a plurality of surface acoustic wave atomisers, in the form of a first surface acoustic wave atomiser 102 and a second acoustic wave atomiser 103. The aerosol-generator 100 further comprises an atomisation region 104 and a supply element 105 for supplying a liquid aerosol-forming substrate to the atomisation region 104.

The first surface acoustic wave atomiser 102 comprises a substrate 106 comprising a sheet of piezoelectric material, and a transducer 107 arranged on an active surface 108 of the substrate 106. The transducer 107 of the first surface acoustic wave atomiser 102 comprises a first array of electrodes 109 and a second array of electrodes 110 interleaved with the first array of electrodes 109. The first and second arrays of electrodes 109, 110 are linear and parallel with each other. During use, the transducer 107 of the first surface acoustic wave atomiser 102 generates surface acoustic waves on the active surface 108 of the substrate 106. The linear shape of the first and second arrays of electrodes 109, 110 results in surface acoustic waves having a linear wavefront directed towards the atomisation region 104.

The second surface acoustic wave atomiser 103 comprises a substrate 111 comprising a sheet of piezoelectric material, and a transducer 112 arranged on an active surface 113 of the substrate 111. The transducer 112 of the second surface acoustic wave atomiser 103 comprises a first array of electrodes 114 and a second array of electrodes 115 interleaved with the first array of electrodes 114. The first and second arrays of electrodes 114, 115 are linear and parallel with each other. During use, the transducer 112 of the second surface acoustic wave atomiser 103 generates surface acoustic waves on the active surface 113 of the substrate 111. The linear shape of the first and second arrays of electrodes 114, 115 results in surface acoustic waves having a linear wavefront directed towards the atomisation region 104.

The substrates 106, 111 of the first and second surface acoustic wave atomisers 102, 103 are arranged to abut each other at one end, and are secured together with adhesive (not shown). Where the substrates 106, 111 abut each other, the substrates 106, 111 define an opening in the active surfaces 108, 113, which forms the atomisation region 104. In this embodiment, each of the substrates 106, 111 has a planar shape, and the substrates 106, 111 are arranged in a common plane, as shown in FIG. 2. The first and second surface acoustic wave atomisers 102, 103 are substantially identical, and are oriented in opposing directions, such that the first acoustic wave atomiser 102 generates surface acoustic waves on the active surface 108 in a first direction towards the atomisation region 104, and the second surface acoustic wave atomiser 103 generates surface acoustic waves on the active surface 113 in a second direction towards the atomisation region, the second direction being parallel and opposite to the first direction.

The supply element 105 is arranged between the substrates 106, 111 of the first and second surface acoustic wave atomisers 102, 103, and the supply element 105 comprises a channel 116 extending through the substrates 106, 111. An inlet 117 of the channel 116 is formed between a passive surface 118 of the substrate 106 of the first surface acoustic wave atomiser 102 and a passive surface 119 of the substrate 111 of the second surface acoustic wave atomiser 103. An outlet 120 of the channel 116 is formed between the active surface 108 of the first surface acoustic wave atomiser 102 and the active surface 113 of the second surface acoustic wave atomiser 103. In this embodiment, the outlet 120 has a square shape, with an axis parallel to the first and second directions. The channel 116 extends between the inlet 117 and the outlet 120. The outlet 120 is positioned within the atomisation region 104. During use, a liquid aerosol-forming substrate is supplied to the atomisation region 104 through the channel 116, where it is atomised by surface acoustic waves generated by the first and second transducers 107, 112.

As shown in FIGS. 2 and 3, the channel 116 has a cross-sectional area that varies in a direction from the inlet 117 to the outlet 120. In particular, the channel 116 has a curved wedge shape so that the cross-sectional area of the channel 116 increases in the direction from the inlet 117 to the outlet 120. The smaller cross-sectional area of the channel 116 at the inlet 117 facilitates control of the flow rate of liquid aerosol-forming substrate into the channel 116. The larger cross-sectional area of the channel 116 at the outlet 120 provides a larger surface area of liquid aerosol-forming substrate at the atomisation region 104 to facilitate atomisation of the liquid aerosol-forming substrate. A curved transition is provided between the active surfaces 108, 113 and the channel 116, which facilitates the transfer of energy from the surface acoustic waves to the liquid aerosol-forming substrate in the atomisation region 104.

Figure 4:
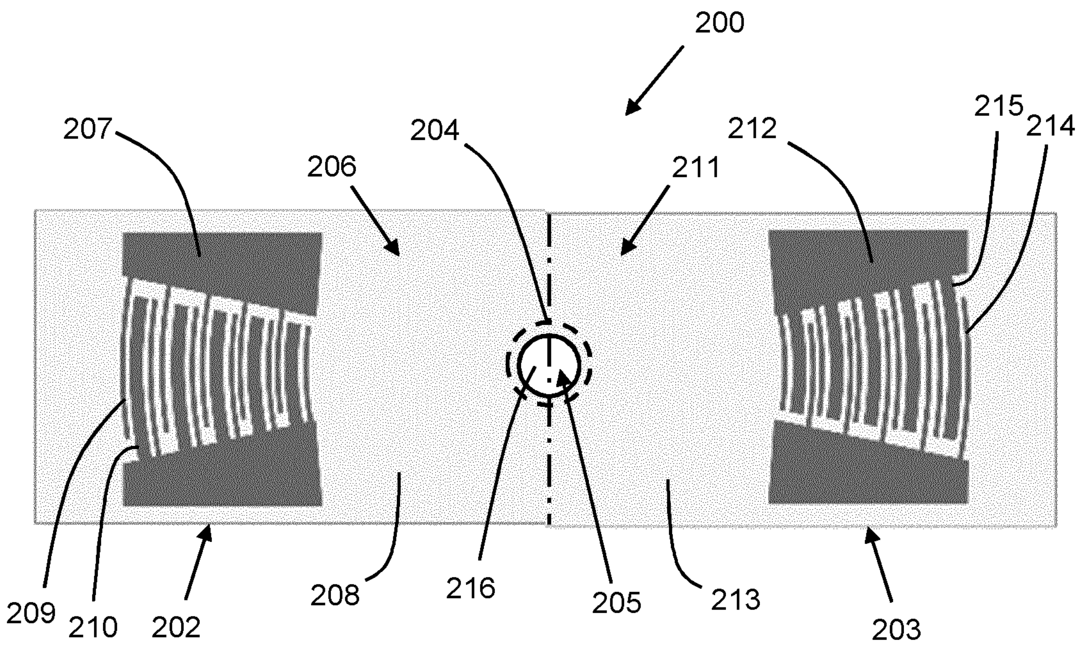
FIG. 4 shows a top view of an aerosol-generator according to a second embodiment of the present disclosure.
Figure 5:
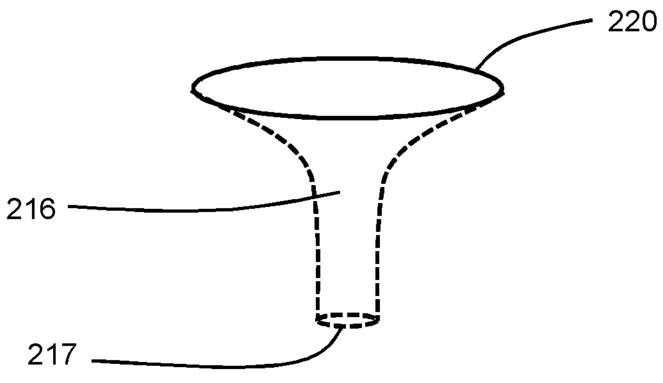
FIG. 5 shows a perspective view of the channel of the aerosol-generator of FIG. 4.

FIGS. 4 and 5 show an aerosol-generator 200 according to a second embodiment of the present disclosure. The aerosol-generator 200 comprises a plurality of surface acoustic wave atomisers, in the form of a first surface acoustic wave atomiser 202 and a second acoustic wave atomiser 203. The aerosol-generator 200 further comprises an atomisation region 204 and a supply element 205 for supplying a liquid aerosol-forming substrate to the atomisation region 204.

The first surface acoustic wave atomiser 202 comprises a substrate 206 comprising a sheet of piezoelectric material, and a transducer 207 arranged on an active surface 208 of the substrate 206. The transducer 207 of the first surface acoustic wave atomiser 202 comprises a first array of electrodes 209 and a second array of electrodes 210 interleaved with the first array of electrodes 209. The first and second arrays of electrodes 209, 210 are curved and parallel with each other. During use, the transducer 207 generates surface acoustic waves on the active surface 208 of the substrate 206. The curved shape of the first and second arrays of electrodes 209, 210 results in surface acoustic waves having a concave wavefront focused towards the atomisation region 204.

The second surface acoustic wave atomiser 203 comprises a substrate 211 comprising a sheet of piezoelectric material, and a transducer 212 arranged on an active surface 213 of the substrate 211. The transducer 212 of the second surface acoustic wave atomiser 203 comprises a first array of electrodes 214 and a second array of electrodes 215 interleaved with the first array of electrodes 214. The first and second arrays of electrodes 214, 215 are curved and parallel with each other. During use, the transducer 212 generates surface acoustic waves on the active surface 213 of the substrate 211. The curved shape of the first and second arrays of electrodes 214, 215 results in surface acoustic waves having a concave wavefront focused towards the atomisation region 204.

The substrates 206, 211 of the first and second surface acoustic wave atomisers 202, 203 are arranged to abut each other at one end, and are secured together with adhesive (not shown). Where the substrates 206, 211 abut each other, the substrates 206, 211 define an opening in the active surfaces 208, 213, which forms the atomisation region 204. In this embodiment, each of the substrates 206, 211 has a planar shape, and the substrates 206, 211 are arranged in a common plane. The first and second surface acoustic wave atomisers 202, 203 are substantially identical, and are oriented in opposing directions, such that the first acoustic wave atomiser 202 generates surface acoustic waves on the active surface 208 in a first direction towards the atomisation region 204, and the second surface acoustic wave atomiser 203 generates surface acoustic waves on the active surface 213 in a second direction towards the atomisation region, the second direction being opposite to the first direction.

The supply element 205 is arranged between the substrates 206, 211 of the first and second surface acoustic wave atomisers 202, 203, and the supply element 205 comprises a channel 216 extending through the substrates 206, 211. An inlet 217 of the channel 216 is formed between a passive surface 218 of the substrate 206 of the first surface acoustic wave atomiser 202 and a passive surface 219 of the substrate 211 of the second surface acoustic wave atomiser 203. An outlet 220 of the channel 216 is formed between the active surface 208 of the first surface acoustic wave atomiser 202 and the active surface 213 of the second surface acoustic wave atomiser 203. In this embodiment, the outlet 220 has a circular shape, with a centre that is the focal point of the concave wavefronts of the surface acoustic waves generated by the transducers 207, 212. The channel 216 extends between the inlet 217 and the outlet 220. The outlet 220 is positioned within the atomisation region 204. During use, a liquid aerosol-forming substrate is supplied to the atomisation region 204 through the channel 216, where it is atomised by surface acoustic waves generated by the first and second transducers 207, 212.

As shown in FIG. 5, the channel 216 has a cross-sectional area that varies in a direction from the inlet 217 to the outlet 220. In particular, the channel 216 has a curved funnel shape so that the cross-sectional area of the channel 216 increases in the direction from the inlet 217 to the outlet 220. A curved transition is also provided between the active surfaces 208, 213 and the channel 216.

Figure 6:
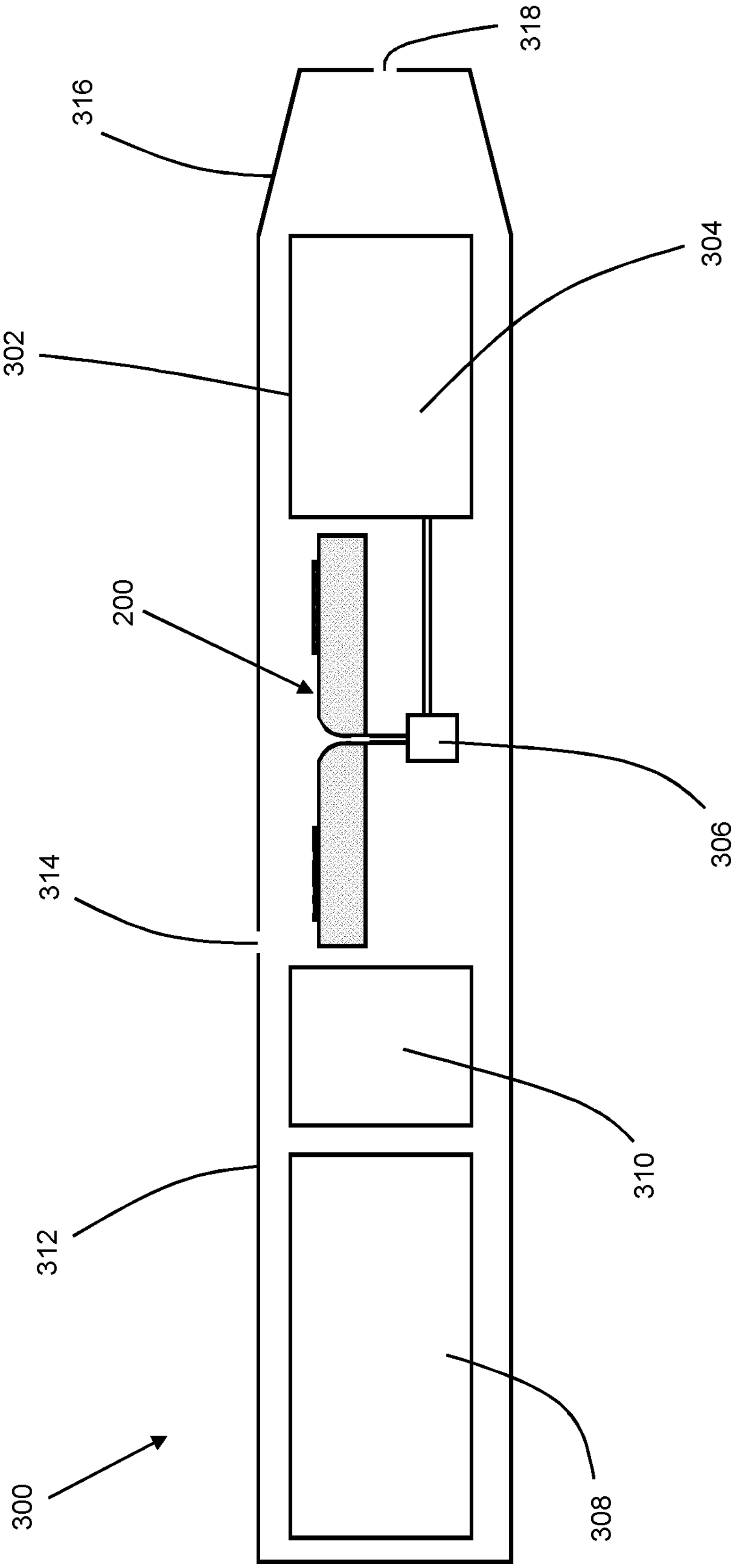
FIG. 6 shows a cross-sectional view of an aerosol-generating device comprising the aerosol-generator of FIGS. 4 and 5.

FIG. 6 shows a cross-sectional view of an aerosol-generating device 300 comprising the aerosol-generator 200. The aerosol-generating device 300 also comprises a liquid storage portion 302 containing a liquid aerosol-forming substrate 304, and a flow control element 306 comprising a micro-pump. The micro-pump is arranged to supply the liquid aerosol-forming substrate 304 from the liquid storage portion 302 to the inlet 217 of the aerosol-generator 200.

The aerosol-generating device 300 also comprises a power supply 308 comprising a rechargeable battery, and a controller 310. The controller 310 is configured to provide control signals to the flow control element 306 to control a flow rate of the liquid aerosol-forming substrate 304 from the liquid storage portion 302 to the inlet 320 of the aerosol-generator 200. The controller 310 is also configured to supply an electrical current from the power supply 308 to the aerosol-generator 200 to drive the first and second transducers 207, 212.

The aerosol-generating device 300 also comprises a housing 312 in which the aerosol-generator 200, the liquid storage portion 302, the flow control element 306, the power supply 308 and the controller 310 are contained. The housing 312 defines an air inlet 314, a mouthpiece 316, and an air outlet 318. During use, a user draws on the mouthpiece 316 to draw air through the housing 312 from the air inlet 314 to the air outlet 318. Aerosol generated by the aerosol-generator 200 is entrained in the airflow through the housing 312 for delivery to the user.

Figure 7:
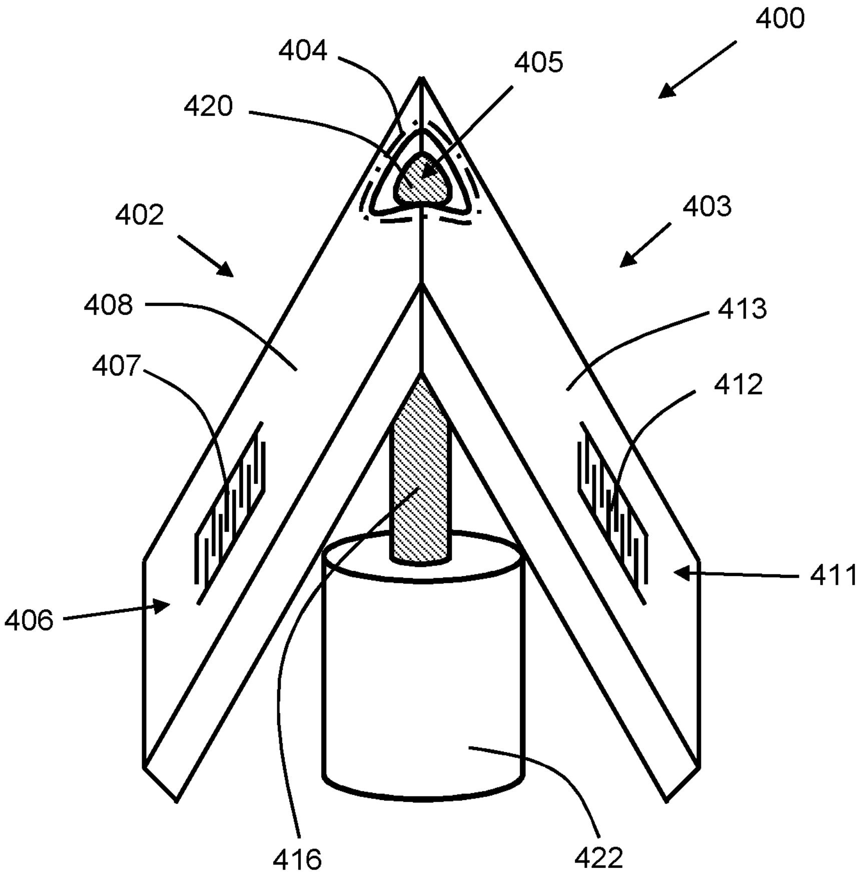
FIG. 7 shows a perspective view of an aerosol-generator according to a third embodiment of the present disclosure.
Figure 8:
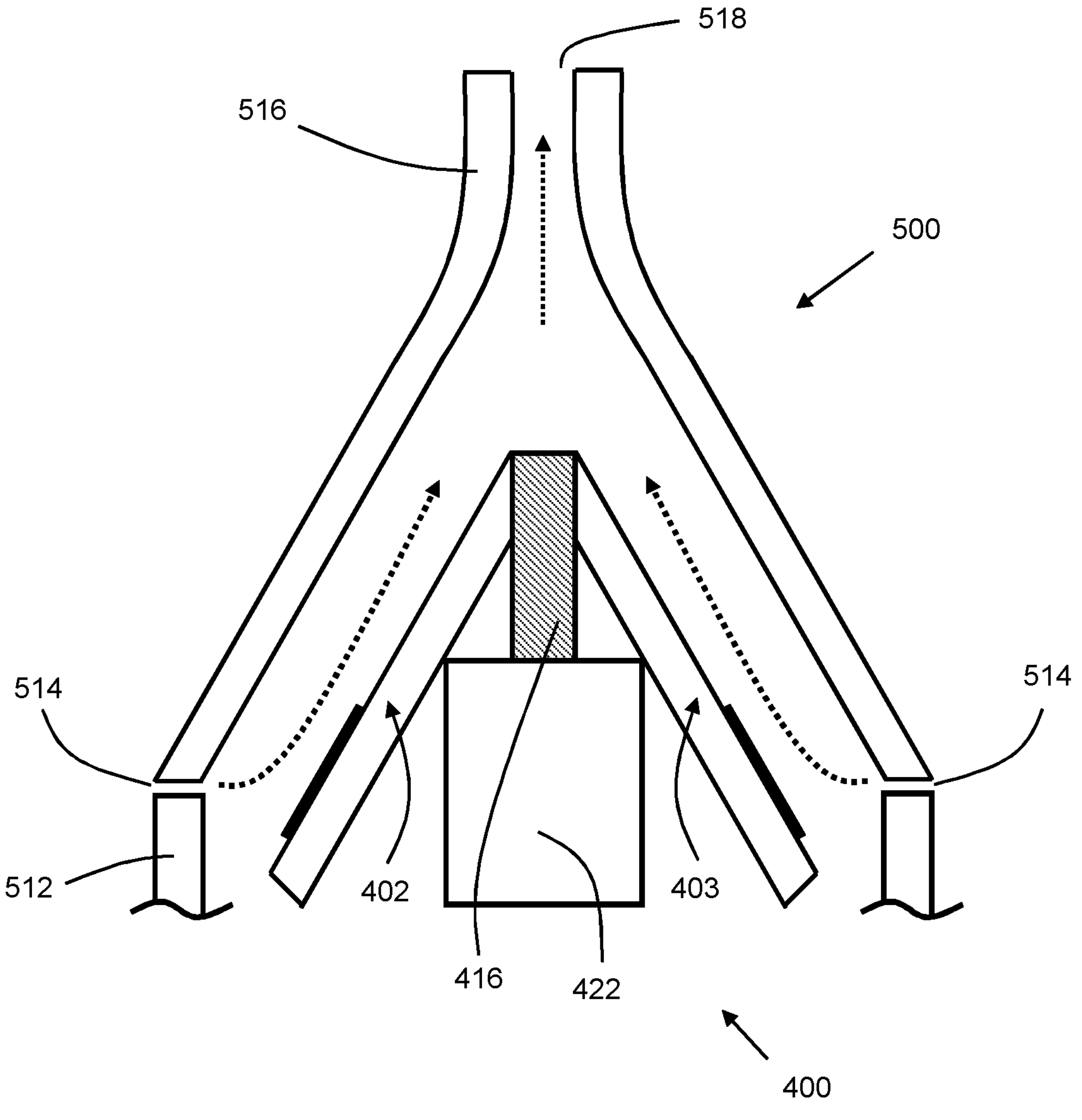
FIG. 8 shows a cross-sectional view of a portion of an aerosol-generating device comprising the aerosol-generator of FIG. 7.

FIGS. 7 and 8 show an aerosol-generator 400 according to a third embodiment of the present disclosure. The aerosol-generator 400 comprises a plurality of surface acoustic wave atomisers, in the form of a first surface acoustic wave atomiser 402 and a second acoustic wave atomiser 403. The aerosol-generator 400 further comprises an atomisation region 404 and a supply element 405 for supplying a liquid aerosol-forming substrate to the atomisation region 404.

The first surface acoustic wave atomiser 402 comprises a substrate 406 comprising a sheet of piezoelectric material, and a transducer 407 arranged on an active surface 408 of the substrate 406. The second surface acoustic wave atomiser 403 comprises a substrate 411 comprising a sheet of piezoelectric material, and a transducer 412 arranged on an active surface 413 of the substrate 411. Each of the first and second transducers 407, 412 comprises first and second arrays of interleaved electrodes as described with respect to the first and second transducers 107, 112 of FIGS. 1, 2 and 3. The first and second arrays of electrodes of each of the first and second transducers 407, 412 are linear and parallel with each other. During use, the transducer 407 of the first surface acoustic wave atomiser 402 generates surface acoustic waves on the active surface 408 of the substrate 406. During use, the transducer 412 of the second surface acoustic wave atomiser 403 generates surface acoustic waves on the active surface 413 of the substrate 411. The linear shape of the arrays of electrodes of the first and second transducers 407, 412 results in surface acoustic waves having a linear wavefront directed towards the atomisation region 404.

The substrates 406, 411 of the first and second surface acoustic wave atomisers 402, 403 are arranged to abut each other at one end, and are secured together at their abutting ends with adhesive (not shown). Where the substrates 406, 411 abut each other, the substrates 406, 411 define an opening 420 in the active surfaces 408, 413, which forms the atomisation region 404. In this embodiment, each of the substrates 406, 411 has a substantially cuboidal shape, and the substrates 406, 411 are arranged in different, non-parallel planes that intersect where the substrates 406, 411 abut. As such, the substrates 606, 411 are arranged in a generally triangular or V-shaped configuration.

In this embodiment, the supply element 405 is a capillary wick 416 that is arranged in the space between the substrates 406, 411, and extends from the opening 420 between the substrates 406, 411 at one end to a liquid reservoir 422 at the opposite end. The liquid reservoir 422 is also arranged in the space between the substrates 406, 411. The liquid reservoir 422 contains a liquid aerosol-forming substrate that is supplied to the atomisation region 404 by the capillary wick 416.

The aerosol-generator 400 is shown arranged in an aerosol-generating device 500 in FIG. 8. The aerosol-generating device 500 comprises a hollow, substantially cylindrical housing 512 defining airs inlet 514, and a mouthpiece 516 having an air outlet 518. The aerosol-generator 400 is arranged within the housing 512, between the air inlets 514 and the mouthpiece 516, such that the air inlets 514 are positioned upstream of the atomisation region 404 and the air outlet 518 is positioned downstream of the atomisation region 404.

During use, a user draws on the mouthpiece 516 to draw air through the housing 512 from the air inlet 514 to the air outlet 518. Aerosol generated by the aerosol-generator 300 is entrained in the airflow through the housing 512 for delivery to the user.

Airflow between the air inlets 514 and the air outlet 518 is shown by the dotted arrows in FIG. 8. The aerosol-generator is positioned such that airflow pathways are defined between the active surfaces 406, 411 of the first and second surface acoustic wave atomisers 402, 403, and internal surfaces of the housing 512. The non-coplanar arrangement of the active surfaces 406, 411 enables the aerosol-generator 400 and the housing 512 to have complementary shapes, which in turn enables the size and shape of the airflow pathways between the aerosol-generator 400 and the housing 512 to be easily controlled during manufacture of the aerosol-generating device 500. Controlling the size and shape of the airflow pathways ensures that the resistance to draw through the device is controlled during manufacture of the aerosol-generating device 500.

FIGS. 9*a*, 9*b* and 9*c* show an aerosol-generator 600 according to a fourth embodiment of the present disclosure. The aerosol-generator 600 comprises a plurality of surface acoustic wave atomisers, in the form of a first surface acoustic wave atomiser 602 and a second acoustic wave atomiser 603. The aerosol-generator 600 further comprises an atomisation region 604 and a supply element 605 for supplying a liquid aerosol-forming substrate to the atomisation region 604.

The first surface acoustic wave atomiser 602 comprises a substrate 606 comprising a sheet of piezoelectric material, and a transducer 607 arranged on an active surface 608 of the substrate 606. The second surface acoustic wave atomiser 603 comprises a substrate 611 comprising a sheet of piezoelectric material, and a transducer 612 arranged on an active surface 613 of the substrate 611. Each of the first and second transducers 607, 612 comprises first and second arrays of interleaved electrodes as described with respect to the first and second transducers 107, 112 of FIGS. 1, 2 and 3. The first and second arrays of electrodes of each of the first and second transducers 607, 612 are linear and parallel with each other. During use, the transducer 607 of the first surface acoustic wave atomiser 602 generates surface acoustic waves on the active surface 608 of the substrate 606. During use, the transducer 612 of the second surface acoustic wave atomiser 603 generates surface acoustic waves on the active surface 613 of the substrate 611. The linear shape of the arrays of electrodes of the first and second transducers 607, 612 results in surface acoustic waves having a linear wavefront directed towards the atomisation region 604.

In this embodiments, each of the first and second surface acoustic wave atomisers 602, 603 comprises a substantially identical substrate 606, 611. Accordingly, only the substrate of the first surface acoustic wave atomiser 602 is described here, and shown in FIGS. 9*b* and 9*c*.

The substrate 606 of the first surface acoustic wave atomiser 602 has a generally rectangular profile, with a generally planar active surface 608. The transducer 607 is arranged towards one end of the active surface 607, and the atomisation region 604 is arranged at the opposite end of the active surface 607.

The substrate 606 also comprises a passive surface 618 opposite to the active surface 606. The passive surface 618 comprises a groove 621 extending centrally along the length of the passive surface 618, from an opening 620 at the end having the atomisation region 604 to a cavity 622 formed at the opposite end of the passive surface 618. The groove 621 forms half of the supply element channel 616 of the aerosol-generator, the other half of the supply element channel 616 being formed by the corresponding groove in the passive surface of the substrate 613 of the second surface acoustic wave atomiser 603. The cavity 622 forms half of a liquid reservoir of the aerosol-generator, the other half of the liquid reservoir being formed by the corresponding cavity in the passive surface of the substrate 613 of the second surface acoustic wave atomiser 603.

An edge portion of the active surface 608 of the substrate 606 of the first acoustic wave atomiser 602, at the atomisation region 604, has a rounded profile, tapering towards the opening 620. The edge portion of the active surface 608 is also curved or rounded towards the passive surface 618. This rounded profile of the substrate 606 towards the opening 620 and the passive surface 618 facilitates delivery of surface acoustic waves from the transducer 607 to the atomisation region 604.

When the first surface acoustic wave atomiser 602 and the second surface acoustic wave atomiser 603 are arranged for use, the substrate 606 of the first surface acoustic wave atomiser 602 overlies the substrate 611 of the second surface acoustic wave atomiser 603 so that the passive surfaces of the substrates 606, 611 are in contact with each other. The groove 621 in the passive surface 618 of the substrate 606 of the first surface acoustic wave atomiser 602 overlies the corresponding groove in the passive surface of the substrate 611 of the second surface acoustic wave atomiser 603 to form a channel 616. The cavity 622 in the passive surface 618 of the substrate 606 of the first surface acoustic wave atomiser 602 overlies the corresponding cavity in the passive surface of the substrate 611 of the second surface acoustic wave atomiser 603 to form a liquid reservoir. The liquid reservoir is configured to hold a supply of liquid aerosol-forming substrate. The channel 616 fluidly connects the liquid reservoir to the opening 620 at the atomisation region 604. Accordingly, the channel 616 forms the liquid supply element. Advantageously, such a configuration of surface acoustic wave atomisers provides a compact aerosol-generator that is straightforward to manufacture.

FIGS. 10*a* and 10*b* show an aerosol-generator 700 according to a fifth embodiment of the present disclosure. The aerosol-generator 700 comprises a plurality of surface acoustic wave atomisers, in the form of six surface acoustic wave atomisers 702. The aerosol-generator 700 further comprises an atomisation region 704 and a supply element 705 for supplying a liquid aerosol-forming substrate to the atomisation region 704.

Each of the surface acoustic wave atomisers 702 are identical, and so only one of the atomisers is described.

The surface acoustic wave atomiser 702 comprises a substrate comprising a sheet of piezoelectric material, and a transducer 707 arranged on an active surface of the substrate. The transducer 707 comprises first and second arrays of interleaved electrodes as described with respect to the first and second transducers 107, 112 of FIGS. 1, 2 and 3. The first and second arrays of electrodes of the transducer 707 are linear and parallel with each other. During use, the transducer 707 generates surface acoustic waves on the active surface of the substrate. The linear shape of the array of electrodes of the transducer 707 results in surface acoustic waves having a linear wavefront directed towards the atomisation region 704.

The substrate of each of the surface acoustic wave atomisers 702 has a generally isosceles trapezoidal prismatic shape, with an active surface having an isosceles trapezoidal shape. The substrates are arranged in a generally truncated hexagonal pyramid, with the long edges of the substrates abutting together. In this embodiment, the long edges of adjacent substrates are secured together with an adhesive (not shown). The shortest edges of each of the substrates together define an opening 720. In this embodiment, the supply element 705 is in the form of a capillary wick, and one end of the capillary wick extends through the opening 720 for delivering liquid aerosol-forming substrate to the opening 720 and the atomisation region 704. Advantageously, such a configuration and arrangement of substrates provides a compact aerosol-generator configuration that is relatively straightforward to manufacture and arrange within an aerosol-generating device.

It will be appreciated that the above described embodiments are example embodiment of the present disclosure, and other arrangements and configurations of features are envisaged in accordance with the present disclosure.

The invention claimed is:

1. An aerosol-generator for an aerosol-generating device, the aerosol-generator comprising:

a plurality of surface acoustic wave atomisers, each surface acoustic wave atomiser comprising:

a substrate comprising an active surface, and at least one transducer disposed on the active surface of the substrate and being configured to generate surface acoustic waves on the active surface;

an atomisation region defined between the substrates of the plurality of surface acoustic wave atomisers; and a supply element arranged to supply a liquid aerosol-forming substrate to the atomisation region.

2. The aerosol-generator according to claim 1, wherein the substrates of the plurality of surface acoustic wave atomisers abut each other to define an opening bounded by the substrates, and wherein the opening forms the atomisation region.

3. The aerosol-generator according to claim 2, wherein each of the at least one transducers is configured to generate surface acoustic waves in a direction towards the opening.

4. The aerosol-generator according to claim 2, wherein each of the substrates has a planar shape.

5. The aerosol-generator according to claim 4, wherein the substrates of the plurality of surface acoustic wave atomisers are disposed in a common plane.

6. The aerosol-generator according to claim 4, wherein the substrates of the plurality of surface acoustic wave atomisers are disposed in a non-coplanar arrangement with respect to each other.

7. The aerosol-generator according to claim 4, wherein the substrates of the plurality of surface acoustic wave atomisers are arranged to form a polyhedral shape.

8. The aerosol-generator according to claim 2, wherein the plurality of surface acoustic wave atomisers comprises at least three surface acoustic wave atomisers.

9. The aerosol-generator according to claim 8, wherein each of the substrates has an isosceles trapezoidal prismatic shape.

10. The aerosol-generator according to claim 9, wherein each of the active surfaces of the substrates has an isosceles trapezoidal shape, and wherein shortest edges of each of the isosceles trapezoidal shapes together define the opening.

11. The aerosol-generator according to claim 2, wherein an edge portion of each of the substrates partially defines the opening, and wherein each edge portion has a square profile, a rounded profile, a triangular profile, or a bevelled profile.

12. The aerosol-generator according to claim 2, wherein the supply element comprises a capillary wick extending into the atomisation region.

13. The aerosol-generator according to claim 1, wherein each of the substrates comprises a passive surface opposite the active surface, and wherein the supply element comprises a groove formed in the passive surface of at least one of the substrates, the groove having an end in fluid communication with the atomisation region.

14. The aerosol-generator according to claim 13, wherein the plurality of surface acoustic wave atomisers further comprises a first surface acoustic wave atomiser comprising a first substrate and a second surface acoustic wave atomiser comprising a second substrate, wherein the first substrate overlies the second substrate so that the passive surfaces of the first substrate and the second substrate are in contact with each other, wherein the supply element comprises a first groove formed in the passive surface of the first substrate and a second groove formed in the passive surface of the second substrate, and wherein the first groove and the second groove overlie each other to form a channel in fluid communication with the atomisation region.

15. An aerosol-generating device, comprising:

an aerosol-generator according to claim 1;

a controller configured to control the at least one transducer of each surface acoustic wave atomiser;

a power supply; and a liquid storage portion configured to receive a liquid aerosol-forming substrate, wherein the supply element is arranged to supply liquid aerosol-forming substrate from the liquid storage portion to the atomisation region.

16. The aerosol-generating device according to claim 15, further comprising a device housing, wherein the aerosol-generator is disposed within the device housing, and wherein the device housing defines at least one air inlet disposed upstream of the atomisation region and at least one air outlet disposed downstream of the atomisation region.

17. The aerosol-generating device according to claim 16, wherein each of the substrates has a planar shape, wherein the substrates of the plurality of surface acoustic wave atomisers are disposed in a non-coplanar arrangement with respect to each other, and wherein the aerosol-generator is arranged within the device housing to define an airflow pathway extending between at least one of the planar substrates and a portion of the device housing.

18. The aerosol-generating device according to claim 16, wherein each of the substrates has a planar shape, wherein the substrates of the plurality of surface acoustic wave atomisers are arranged to form a polyhedral shape, and wherein the aerosol-generator is arranged within the device housing to define an airflow pathway extending between at least one of the planar substrates and a portion of the device housing.

* * * * *